(12) United States Patent
Kendrick et al.

(10) Patent No.: US 12,011,547 B2
(45) Date of Patent: Jun. 18, 2024

(54) WETTING MECHANISM FOR A CATHETER (71) Applicant: CONVATEC LIMITED, Flintshire (GB)

(72) Inventors: Andrew Kendrick, Cheshire (GB); Julie Lambrethsen, Cheshire (GB); Oliver Walter Pfleger, Merseyside (GB); Michal Weber, Cheshire (GB)

(73) Assignee: CONVATEC LIMITED, Flintshire (GB)

( * ) Notice: Subject to any disclaimer, the term of this patent is extended or adjusted under 35 U.S.C. 154(b) by 487 days.

(21) Appl. No.: 17/238,464

(22) Filed: Apr. 23, 2021

(65) Prior Publication Data

US 2021/0346644 A1 Nov. 11, 2021

Related U.S. Application Data (63) Continuation of application No. PCT/GB2021/050980, filed on Apr. 23, 2021.

(30) Foreign Application Priority Data

Apr. 24, 2020 (GB) ...................................... 2006055

(51) Int. Cl.
*A61M 25/00* (2006.01)
(52) U.S. Cl.
CPC ... *A61M 25/002* (2013.01); *A61M 2025/0018* (2013.01); *A61M 2205/0222* (2013.01)
(58) Field of Classification Search
CPC ............ A61M 25/002; A61M 25/0111; A61M 25/0017; A61M 25/0113;

(Continued)

(56) References Cited

U.S. PATENT DOCUMENTS 4,834,711 A 5/1989 Greenfield et al.
5,145,094 A * 9/1992 Perlmutter ........... B65D 47/247
222/521

(Continued)

FOREIGN PATENT DOCUMENTS

EP 3092024 7/2015
EP 3283136 B1 6/2021

(Continued)

OTHER PUBLICATIONS

International Search Report; European Patent Office; International Application No. PCT/GB2021/050980; dated Jul. 30, 2021; 4 pages.

(Continued)

*Primary Examiner* — Adam Marcetich
(74) *Attorney, Agent, or Firm* — Taft Stettinius & Hollister LLP; Ryan O. White; Derek B. Lavender (57) ABSTRACT The invention relates to a wetting mechanism 20 for wetting a tube 12 of a catheter 10. The wetting mechanism 20 includes a housing 16 positioned initially at or proximal to the tip end 13 of the catheter tube 12. The housing 16 comprises a wetting chamber 23 into which at least a portion of the catheter tube 12 is able to be introduced and be moved therethrough to wet the catheter tube 12 in use. The wetting mechanism 20 includes a stopper 26 which is moveable between a first and second positions to prevent or allow the tip end 13 of the catheter tube 12 to be moved through the wetting chamber 23.

27 Claims, 5 Drawing Sheets (58) Field of Classification Search
CPC .. A61M 2210/1089; A61M 2210/1085; A61M 2210/1096; A61M 2210/1092; A61M 2025/0018; A61M 2202/0496; A61M 25/0075; A61M 2025/0079; A61M 39/26; A61M 2039/261; A61M 2039/262; A61M 2039/263; A61M 2039/266; A61M 2039/267; A61M 2039/268
See application file for complete search history.

(56) References Cited

U.S. PATENT DOCUMENTS

| | | | |
|---|---|---|---|
| 5,413,561 A * | 5/1995 | Fischell | A61M 39/20 604/167.01 |
| 5,807,348 A * | 9/1998 | Zinger | A61M 39/045 604/537 |
| 6,979,313 B1 * | 12/2005 | Meek | A61M 25/002 604/98.01 |
| 11,376,395 B2 | 7/2022 | Montes de Oca et al. | |
| 11,420,016 B2 | 8/2022 | Palmer | |
| 11,420,017 B2 | 8/2022 | Hilton et al. | |
| 11,497,886 B2 | 11/2022 | Nielsen et al. | |
| 11,524,097 B2 | 12/2022 | Sellers et al. | |
| 11,529,439 B2 | 12/2022 | O'Mahony et al. | |
| 11,534,573 B2 | 12/2022 | Hannon et al. | |
| 11,534,577 B2 | 12/2022 | House | |
| 11,690,947 B2 | 7/2023 | Goebel | |
| 11,724,008 B2 | 8/2023 | Lundahl et al. | |
| 11,730,557 B2 | 8/2023 | O'Flynn et al. | |
| 11,730,918 B2 | 8/2023 | Farrell et al. | |
| 11,738,169 B2 | 8/2023 | Hickmott et al. | |
| 2005/0256461 A1 * | 11/2005 | DiFiore | A61M 39/26 604/537 |
| 2005/0261637 A1 * | 11/2005 | Miller | A61M 39/26 251/149.3 |
| 2008/0097463 A1 * | 4/2008 | House | A61M 25/002 606/108 |
| 2011/0230864 A1 * | 9/2011 | House | A61M 25/0111 604/544 |
| 2013/0079756 A1 | 3/2013 | House | |
| 2013/0214012 A1 * | 8/2013 | Pils | B65D 47/243 222/524 |
| 2014/0312065 A1 * | 10/2014 | Rohr | B65D 81/3211 222/129 |
| 2016/0213880 A1 * | 7/2016 | O'Flynn | A61M 25/0111 |
| 2018/0078700 A1 | 3/2018 | Eliasson | |
| 2018/0104447 A1 | 4/2018 | Madlung et al. | |
| 2018/0161539 A1 * | 6/2018 | Palmer | A61M 25/0111 |
| 2018/0369474 A1 | 12/2018 | Falleboe et al. | |
| 2019/0105462 A1 | 4/2019 | Schertiger | |
| 2019/0201659 A1 | 7/2019 | Gustavsson et al. | |
| 2019/0375525 A1 * | 12/2019 | van Winden | B65B 31/047 |
| 2020/0001049 A1 * | 1/2020 | House | A61M 25/0111 |
| 2020/0155261 A1 | 5/2020 | O'Flynn et al. | |
| 2020/0222659 A1 | 7/2020 | Schertiger et al. | |
| 2021/0162180 A1 | 6/2021 | Gershbaum | |
| 2021/0196923 A1 | 7/2021 | Palmer | |
| 2021/0228836 A1 | 7/2021 | Terry | |
| 2021/0260332 A1 | 8/2021 | Panesar et al. | |
| 2021/0275727 A1 | 9/2021 | Farrell et al. | |
| 2021/0290893 A1 * | 9/2021 | Palmer | A61M 27/00 |
| 2021/0290895 A1 | 9/2021 | Nielsen et al. | |
| 2021/0330929 A1 | 10/2021 | Kendrick et al. | |
| 2021/0330938 A1 | 10/2021 | Kendrick et al. | |
| 2021/0346644 A1 | 11/2021 | Kendrick et al. | |
| 2021/0346647 A1 | 11/2021 | Kendrick et al. | |
| 2021/0346648 A1 | 11/2021 | Kendrick et al. | |
| 2021/0353449 A1 | 11/2021 | Sharma et al. | |
| 2021/0370019 A1 | 12/2021 | Erbey et al. | |
| 2022/0001136 A1 | 1/2022 | Hede et al. | |
| 2022/0001139 A1 | 1/2022 | Eriksson et al. | |
| 2022/0008626 A1 | 1/2022 | Farrell et al. | |
| 2022/0023585 A1 | 1/2022 | Schertiger et al. | |
| 2022/0054295 A1 | 2/2022 | Becker | |
| 2022/0118161 A1 | 4/2022 | Bager et al. | |
| 2022/0126057 A1 | 4/2022 | Eriksson et al. | |
| 2022/0133426 A1 | 5/2022 | O'Flynn et al. | |
| 2022/0134054 A1 | 5/2022 | Schertiger et al. | |
| 2022/0176068 A1 | 6/2022 | Pfleger et al. | |
| 2022/0176069 A1 | 6/2022 | Jenco et al. | |
| 2022/0211973 A1 | 7/2022 | Palmer | |
| 2022/0226602 A1 | 7/2022 | Farrell | |
| 2022/0226604 A1 | 7/2022 | Murray et al. | |
| 2022/0233808 A1 | 7/2022 | Farrell et al. | |
| 2022/0241549 A1 | 8/2022 | Murray et al. | |
| 2022/0241553 A1 | 8/2022 | Farrell et al. | |
| 2022/0249805 A1 | 8/2022 | Pedersen | |
| 2022/0280751 A1 | 9/2022 | Farrell et al. | |
| 2022/0288350 A1 | 9/2022 | Montes de Oca et al. | |
| 2022/0347354 A1 | 11/2022 | Sileika et al. | |
| 2022/0347430 A1 | 11/2022 | Pedersen | |
| 2022/0370688 A1 | 11/2022 | Sileika et al. | |
| 2022/0370689 A1 | 11/2022 | Sileika et al. | |
| 2022/0379075 A1 | 12/2022 | Hilton et al. | |
| 2022/0387673 A1 | 12/2022 | Farrell et al. | |
| 2022/0409859 A1 | 12/2022 | Sileika et al. | |
| 2023/0241288 A1 | 8/2023 | O'Mahony et al. | |

FOREIGN PATENT DOCUMENTS

| | | |
|---|---|---|
| EP | 3854427 A1 | 7/2021 |
| EP | 3854438 A1 | 7/2021 |
| EP | 3338827 B1 | 8/2021 |
| EP | B862031 A1 | 8/2021 |
| EP | 3519031 B1 | 9/2021 |
| EP | 2750749 B1 | 10/2021 |
| EP | 3184140 B1 | 10/2021 |
| EP | 3668555 B1 | 10/2021 |
| EP | 3727550 B1 | 10/2021 |
| EP | 3892320 A1 | 10/2021 |
| EP | 3897480 A1 | 10/2021 |
| EP | 3921009 A1 | 12/2021 |
| EP | 3930815 A1 | 1/2022 |
| EP | 3932438 A1 | 1/2022 |
| EP | 3943140 A1 | 1/2022 |
| EP | 3952973 A1 | 2/2022 |
| EP | 3955863 A1 | 2/2022 |
| EP | 3082929 B1 | 3/2022 |
| EP | 3983023 A1 | 4/2022 |
| EP | 3725355 B1 | 5/2022 |
| EP | 3990084 A1 | 5/2022 |
| EP | 3990085 A1 | 5/2022 |
| EP | 3991773 A1 | 5/2022 |
| EP | 3727549 B1 | 6/2022 |
| EP | 4015008 A1 | 6/2022 |
| EP | 2515988 B2 | 7/2022 |
| EP | 2968842 B1 | 7/2022 |
| EP | 3897766 B1 | 7/2022 |
| EP | 4021549 A1 | 7/2022 |
| EP | 3593850 B1 | 9/2022 |
| EP | 3821934 B1 | 9/2022 |
| EP | 4051328 A1 | 9/2022 |
| EP | 4051329 A1 | 9/2022 |
| EP | 4051330 A1 | 9/2022 |
| EP | 4051358 A1 | 9/2022 |
| EP | 4061463 A1 | 9/2022 |
| EP | 3257546 B1 | 10/2022 |
| EP | 4085962 A1 | 11/2022 |
| EP | 4088749 A1 | 11/2022 |
| EP | 2688629 B1 | 12/2022 |
| EP | 3308823 B1 | 12/2022 |
| EP | 3793626 B1 | 12/2022 |
| EP | 4101492 A1 | 12/2022 |
| EP | 2908898 B1 | 7/2023 |
| EP | 3148625 B1 | 7/2023 |
| EP | 3651844 B1 | 7/2023 |
| EP | 3119464 B2 | 8/2023 |
| EP | 3921009 B1 | 8/2023 |
| EP | 3990085 B1 | 8/2023 |
| EP | 3421071 B1 | 9/2023 |
| EP | 3883630 B1 | 9/2023 |
| EP | 4241818 A2 | 9/2023 |
| EP | 4245349 A2 | 9/2023 |

(56) References Cited

FOREIGN PATENT DOCUMENTS

| | | | |
|---|---|---|---|
| GB | 2540125 | B | 1/2017 |
| GB | 2596593 | A | 1/2022 |
| KR | 1020160092786 | A | 8/2016 |
| WO | 2021183718 | A1 | 9/2021 |
| WO | 2021219188 | A1 | 11/2021 |
| WO | 2021228341 | A1 | 11/2021 |
| WO | 2021231724 | A1 | 11/2021 |
| WO | 2021240266 | A1 | 12/2021 |
| WO | 2021242487 | A1 | 12/2021 |
| WO | 2021242676 | A1 | 12/2021 |
| WO | 2021242745 | A1 | 12/2021 |
| WO | 2022002483 | A1 | 1/2022 |
| WO | 2022003619 | A1 | 1/2022 |
| WO | 2022031550 | A1 | 2/2022 |
| WO | 2022090055 | A1 | 5/2022 |
| WO | 2022108750 | A1 | 5/2022 |
| WO | 2022118010 | A1 | 6/2022 |
| WO | 2022118011 | A1 | 6/2022 |

OTHER PUBLICATIONS

Written Opinion of the International Searching Authority; European Patent Office; International Application No. PCT/GB2021/050980; dated Jul. 30, 2021; 6 pages.

\* cited by examiner

WETTING MECHANISM FOR A CATHETER

This application is a continuation of International Application No. PCT/GB2021/050980 filed Apr. 23, 2021 and claims the priority of GB Application No. 2006055.4, filed Apr. 24, 2020. The disclosures of which are hereby incorporated herein in their entirety.

TECHNICAL FIELD OF THE INVENTION

The present invention relates to a wetting mechanism for a catheter (e.g. a urinary catheter) for wetting a tube of the catheter, in use. The invention extends to a catheter comprising the wetting mechanism and a method for wetting a catheter tube.

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc. remain open. Urinary catheters are designed for use for insertion into a user's bladder via the urethra to drain the bladder.

To maximise comfort and minimise the risk of trauma and/or infection, an outer surface of the catheter tube is typically wetted using a wetting fluid prior to insertion by the user. In further developments, the catheter tube itself comprises, is integrated with or is coated with a hydrophilic component (e.g. a hydrophilic polymer) which serves to reduce friction further upon application of the wetting fluid.

Some catheters may be supplied pre-wetted in a packaging, for instance, where the catheter is at least partially submerged within wetting fluid within the packaging. Whilst this may ensure the catheter tube is adequately wetted prior to use, such arrangements suffer in that components of the catheter other than the catheter tube such as a gripper element or funnel can also become wetted. This has a detrimental effect of the experience of the user where it may become difficult to hold and direct the catheter tube as required. This is particularly problematic where the user is performing self-catheterisation. Further, having the catheter submerged may effectively reduce the shelf-life of the catheter due to long-term exposure of components of the catheter to moisture.

It is therefore seen advantageous to provide a catheter which may be wetted at or immediately prior to the point of use.

In an attempt to address this, some catheters are provided in packaging which includes a rupturable container or sachet within the packaging which a user may burst to release the wetting fluid. Typically, this involves the user squeezing the packaging to cause the container/sachet to break. However, such arrangements experience similar problems to those discussed above where the wetting fluid is allowed to come into contact with other components of the catheter. Such arrangements also result in the possibility of the catheter tube not being fully wetted, or indeed wetted at all, prior to use. This can be harmful for the user. Catheter tubes in such arrangements are also generally exposed upon opening of the packaging which poses an infection risk.

It would therefore be advantageous to provide a catheter which includes a means of supplying a wetting fluid solely to the catheter tube to improve user experience.

It would also be advantageous to provide a system which mitigates the possibility of the catheter tube being used prior to or without adequate lubrication.

It would also be advantageous to provide a system which reduces the infection risk by preventing exposure of the catheter tube prior to use.

It is an aim of an embodiment or embodiments of the invention to overcome or at least partially mitigate one or more problems with the prior art.

SUMMARY OF THE INVENTION

According to an aspect of the invention there is provided a wetting mechanism for wetting a tube of a catheter, the wetting mechanism comprising: a housing configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a moveable stopper configured to prevent or to allow movement of the catheter tube through the wetting chamber.

According to an aspect of the invention there is provided a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber.

Advantageously, the wetting mechanism of the present invention requires a positive action to "unlock" the catheter tube. This may prevent or at least reduce the likelihood of inadvertent activation or exposure of the catheter tube prior to the point of use by the user. Requiring the catheter tube to be moved through the wetting chamber thereby wetting the catheter tube may ensure that the catheter may only be exposed (e.g. by moving the tube out of the housing) once the outer surface of the tube has been adequately wetted.

The housing may advantageously form a separate and moveable (e.g. with respect to the catheter tube and/or other components of the catheter—e.g. a funnel) component of the catheter which acts as a gripping element in both handling the catheter whilst wetting the catheter tube, and handing the catheter whilst positioning and subsequently inserting the catheter tube into the urethra, in use. Having the wetting mechanism configured as part of a gripping element for the catheter improves the usability of the catheter in terms of both the wetting action and ultimately the use of the catheter. For instance, the gripping element may be moved relative to the catheter tube—i.e. along the tube to move the tube through the wetting chamber (thereby wetting the tube and exposing the tip end of the catheter tube), rather than in the prior art solutions where the catheter tube may need to be pushed or pulled through a wetting device, thereby mitigating problems caused by the length of the catheter tube of a male catheter. Furthermore, the gripping element can be used to hold the catheter tube close to the urethra to help a user guide the catheter tube without having to touch the tube itself, thereby mitigating potential contamination issues.

When used herein and throughout the specification the term "prevent" is intended to cover prevention of the associated action during normal use of the wetting mechanism. Specifically, the stopper being configured to prevent movement of the catheter tube should and would be interpreted by the skilled person to cover preventing movement of catheter tube during normal use of the catheter/wetting mechanism. For example, the skilled person would appreciate that the term "prevent" in this instance is not intended to exclude the stopper not restricting movement as a result of misuse of the wetting mechanism/catheter by the user—e.g. a user forcefully moving the catheter tube against the restriction provided by the stopper—but is intended to cover preventing movement of the catheter tube during normal use—e.g. during handling by the user and/or packaging and transporting of the catheter.

Optional features set out below may apply to any aspect of the invention as appropriate.

The tip end of the catheter tube may, at least initially, be disposed outside the wetting chamber. The tip end of the catheter tube may, at least initially, be held within an inlet of the wetting chamber.

The stopper may be linearly moveable between first and second positions. For example, in use, the stopper may be pushed or pulled by a user to move the stopper between the first and second positions.

The stopper may be rotatable. The stopper may be rotatable between first and second angular positions. The first and second angular positions may correspond to the first and second positions of the stopper. The stopper may be threaded, and may be provided within the wetting mechanism through interaction with a complementary threaded surface of the wetting mechanism, for example a complementary threaded surface provided on or within the wetting chamber of the housing.

The stopper may comprise a plug. The plug may be configured to be at least partly withdrawn from the wetting mechanism. The plug may be configured to be at least partly withdrawn from the wetting chamber of the wetting mechanism. Partial withdrawal of the plug may correspond to movement of the plug from the first position to the second position. The plug may be configured to be only partly withdrawn from the wetting mechanism—i.e. it cannot be fully withdrawn from the wetting mechanism. It may remain attached or otherwise coupled to the housing whether in the first or second position. In embodiments, the plug may be configured to be fully withdrawn from the wetting mechanism (optionally from the wetting chamber of the wetting mechanism).

The wetting chamber may comprise an inlet through which the catheter tube is able to be introduced into the wetting chamber. The stopper may block, or at least partially block the inlet in the first position. In some embodiments the wetting mechanism may be configured such that movement of the stopper from the first position to the second position unblocks the inlet, thereby allowing for the catheter tube to be introduced into the wetting chamber (and be moved therethrough).

In embodiments, at least a portion of the stopper may be received within the inlet of the wetting chamber with the stopper in the first position. In this way, the stopper may block or reduce the size of the inlet when in the first position, preventing the tip end of the catheter tube being introduced and moved through the wetting chamber.

In some embodiments an end of the stopper may be received with the inlet of the wetting chamber with the stopper in the first position. The end of the stopper may comprise a flexible and/or compressible material. The flexible and/or compressible material may be configured to be compressed within the inlet of the wetting chamber.

The end may comprise one or more cantilevered portions which may bend or flex when at least partially received within the inlet of the wetting chamber. The one or more cantilevered portions may bend or flex upon interaction with a portion of the housing, for example when being moved into position within the inlet, which may occur, for example, when moving the stopper from the second position to the first position. The end may comprise a plurality of cantilevered portions. The plurality of cantilevered portions may bend or flex in a direction substantially towards one another when at least partially received within the inlet of the wetting chamber.

One particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber; wherein the wetting chamber comprises an inlet through which the catheter tube is able to be introduced into the wetting chamber, and wherein the stopper at least partially blocks the inlet in the first position; wherein an end of the stopper is received with the inlet of the wetting chamber with the stopper in the first position; and wherein the end comprises one or more cantilevered portions operable to bend or flex when at least partially received within the inlet of the wetting chamber.

Another particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber; wherein the wetting chamber comprises an inlet through which the catheter tube is able to be introduced into the wetting chamber, and wherein the stopper at least partially blocks the inlet in the first position; wherein an end of the stopper is received with the inlet of the wetting chamber with the stopper in the first position; and wherein the end of the stopper comprises a plurality of cantilevered portions, the plurality of cantilevered portions being configured to bend or flex in a direction substantially towards one another when at least partially received within the inlet of the wetting chamber.

In an alternative to blocking the inlet, the stopper could be operable to act on a portion of the inlet, e.g. a flexible, tubular portion to restrict its size and thereby prevent movement of the catheter tube in the first position. In the second position, the stopper may allow the portion to expand and thereby allow movement of the catheter tube.

In embodiments, in use, movement of the stopper from the first position to the first second may withdraw the end of the stopper from the inlet of the wetting chamber. Withdrawal of the stopper may release any external force provided on the end of the stopper (e.g. from the housing) and allow the compressed, bent or flexed portion of the stopper to move (e.g. under a biasing force arising from said compression, bending or flexing) to a position where it does not prevent the tip end of the catheter tube from being introduced into the wetting chamber. For example, withdrawal of the stopper may remove any blocking of the inlet of the wetting chamber.

In embodiments, the stopper may be tubular. The tubular stopper may define a channel therethrough. The catheter tube may be moved through said channel, in use. For example, in some embodiments, in the first position, an end of the tubular stopper may be received and optionally compressed within the inlet of the wetting chamber. This may prevent introduction of the tip end of the catheter tube into the channel of the stopper, thereby preventing introduction of the tip end of the catheter tube into and through the wetting chamber of the housing.

One particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber; wherein the stopper is tubular defining a channel therethrough, and wherein the catheter tube may be moved through said channel, in use.

In some embodiments the wetting chamber may comprise an outlet through which the catheter tube is able to exit the wetting chamber. In embodiments wherein the stopper comprises a tubular stopper with a channel therethrough, a first end of the stopper may be positioned at or proximal to the inlet of the wetting chamber and a second end of the stopper may be positioned at or proximal to the outlet of the wetting chamber.

In embodiments, the wetting chamber comprises a volume of fluid contained therein. In such embodiments, the wetting mechanism is configured such that, in use, the catheter tube may be moved through the wetting chamber in contact with said wetting fluid, thereby wetting the outer surface of the catheter tube.

In embodiments, the housing may comprise a holding chamber. The holding chamber may contain a volume of fluid therein. In some embodiments the stopper forms a fluid release control component for the wetting mechanism. Specifically, in some embodiments the stopper may be configured to control release of fluid contained within the holding chamber, e.g. through an opening within the holding chamber. The stopper may be configured to control release of the fluid from the holding chamber to the wetting chamber.

One particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber; wherein the housing comprises a holding chamber containing a volume of fluid therein.

Another particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber; wherein the housing comprises a holding chamber containing a volume of fluid therein; and wherein the stopper forms a fluid release control component for the wetting mechanism configured to control release of fluid contained within the holding chamber to the wetting chamber.

Another particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber; wherein the housing comprises a holding chamber containing a volume of fluid therein; wherein the stopper forms a fluid release control component for the wetting mechanism configured to control release of fluid contained within the holding chamber to the wetting chamber; and wherein the stopper is configured such that, in the first position, the stopper prevents release of fluid from the holding chamber, and in the second position, the stopper allows release of fluid from the holding chamber into the wetting chamber.

The housing—e.g. the wetting chamber and/or in embodiments the holding chamber—may be configured to hold up to 0.25 ml, or up to 0.5 ml, or up to 0.75 ml, or up to 1.0 ml, or up to 1.5 ml, or up to 2.0 ml, or up to 2.5 ml, or up to 3.0 ml, or up to 4.0 ml, or up to 5.0 ml, or up to 7.5 ml, or up to 10 ml of wetting fluid, for example.

In embodiments, the stopper is configured such that, in the first position, the stopper prevents release of fluid from the holding chamber. The stopper may be configured such that, in the second position, the stopper allows release of fluid from the holding chamber into the wetting chamber. For example, movement of the stopper from the first position to the second position may unblock an opening within the holding chamber allowing fluid to flow therethrough.

Advantageously, controlling the release of the fluid from a holding chamber where it is held out of contact with other components of the catheter system overcomes issues with the prior art, particularly where catheters may be disadvantageously submerged in wetting fluid prior to use. It may also improve the shelf life of the catheter by reducing the exposure of most of the components of the catheter to moisture until (or as close as possible to) the point of use. Further, controlling the release of the wetting fluid into a wetting chamber through which the catheter tube may be moved through provides greater control over the application of the wetting fluid to the external surface of the catheter tube. This may ensure the whole surface of the catheter tube is adequately wetted prior to use by the user. Further, having the fluid released at the same time as releasing any block on the movement of the catheter ensures that the catheter tube cannot be moved through the housing (and thereby used) without the wetting fluid being released (and hence the outer surface of the catheter tube wetted).

The wetting mechanism may be configured to retain the stopper in the first and/or second position.

For example, in some embodiments the wetting mechanism may be configured to retain the stopper in the first position unless positively acted on by a user. Advantageously, this may prevent or at least reduce the likelihood of stopper being moved inadvertently, and the catheter tube being exposed prematurely. This may ensure that the catheter tube is wetted at or as close as possible to the point of use to ensure the surface of the catheter tube is fully wetted. In such embodiments, the stopper may be biased to the first position, and the user may be required to act against said bias to move the stopper to the second position. At least a portion of the stopper may abut a further component of the wetting mechanism, e.g. a lip, projection or the like from a surface of the housing preventing movement of the stopper from the first position unless acted on by a user. The abutment may be provided between a frangible portion on the stopper and/or on the housing configured to break upon application of a force by the user. For example, the abutment between the stopper and the further component may be configured such that application of a force (e.g. the user pulling the stopper away from the housing), may be sufficient to overcome said abutment, allowing the plug to be moved to the second position. The stopper may "snap" or "click" in overcoming said abutment to provide tactile and/or audible feedback for the user.

In embodiments, the wetting mechanism may be configured to retain the stopper in the second position, preventing the stopper being returned to the first position. Advantageously, once activated, the wetting mechanism may be configured to be retained in a "used" configuration, ensuring that the catheter and wetting mechanism cannot be returned to a configuration which appears as though it has not been used—i.e. a configuration which suggests that the wetting mechanism may still be operable to wet the catheter tube (which may not be the case). This may prevent or at least reduce the likelihood of the user re-using the catheter (either mistakenly or intentionally). In such embodiments, the wetting mechanism may be configured such that, in the second configuration at least a portion of the stopper is provided in an abutting relationship with a further component of the wetting mechanism (e.g. the housing) preventing further movement of the stopper.

In some embodiments the wetting mechanism comprises a wetting applicator. The wetting applicator may be positioned within the wetting chamber. The wetting applicator may be configured to hold wetting fluid. In embodiments this may comprise wetting fluid released into the wetting chamber from the holding chamber. The wetting applicator may be configured to control application of the fluid to the catheter tube, in use, as the catheter tube is moved through the wetting chamber.

One particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to wet the catheter tube in use; and wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber; the wetting mechanism comprising a wetting applicator positioned within the wetting chamber, the wetting applicator being configured to hold wetting fluid and to control application of the fluid to the catheter tube, in use, as the catheter tube is moved through the wetting chamber.

The wetting applicator may comprise an absorbent material. For example, in some embodiments the wetting applicator comprises a sponge, foam or wicking material, operable to absorb the wetting fluid, in use. In further embodiments, the wetting applicator may comprise a baffle arrangement. The baffle arrangement may define a plurality of subregions of the wetting applicator each configured to hold a portion of the fluid held within the wetting applicator.

The wetting applicator may define a channel within the wetting chamber. The wetting applicator may define a channel within the wetting chamber through which the catheter tube is able to be moved through, in use. The wetting mechanism may be configured such that the catheter tube is moved in contact with the wetting applicator as it is moved through the wetting chamber (e.g. along the channel defined by the wetting applicator. In embodiments, the wetting applicator may be configured such that fluid held within the wetting applicator is able to be released, and preferably is automatically released, therefrom upon movement of the catheter tube through the wetting chamber.

In embodiments, the housing may form a gripping element of the catheter. In use, the gripping element may be used by a user to control application of the catheter. For example, the gripping element can be used to hold the catheter tube close to the urethra to help a user guide the catheter tube without having to touch the tube itself. In embodiments, the housing may comprise a conical profile. A conical profile may be advantageous where there housing forms a gripping element of the catheter.

In embodiments wherein the stopper comprises a plug, the plug may comprise a conical profile. The plug may comprise a hollow or substantially hollow interior. Where combined with a conical profile, such a plug may form a cup shape element which may assist a user with locating the catheter tube, in use. The cup can, for example, be used to locate the housing over the tip of a penis such that the catheter tube can be easily inserted into the urethra immediately after wetting.

In some embodiments, the housing and the plug both comprise a conical profile. In such embodiments, the wetting mechanism may be configured such that, together, the housing and the plug form a substantially hourglass-shaped profile. An hourglass-shaped profile may be particularly advantageous in that it may allow the user to operate the wetting mechanism—i.e. to remove (or at least partially remove) the plug from the housing using only one hand.

According to an aspect of the invention there is provided a catheter, comprising: a catheter tube having a tip end and a distal end; and the wetting mechanism of any preceding aspect operably coupled at or proximal to the tip end of the catheter tube for wetting the catheter tube, in use.

The catheter may comprise a funnel. The funnel may be provided at or proximal to the distal end of the catheter tube. The funnel may comprise a fluid outlet for the discharge of fluid from within the catheter tube.

In embodiments, the catheter comprises a sleeve. The sleeve may be positioned about the catheter tube. In embodiments, the sleeve may define an internal volume about at least a portion of the catheter tube. The sleeve may comprise a flexible material. The sleeve may be thin and readily crumpled. For example, the sleeve may be formed of a film of plastics material, which may be low-density polyethylene, for example.

The sleeve may be coupled to the wetting mechanism. For example, the sleeve may be coupled at a first end to the wetting mechanism. In such embodiments, the sleeve may be coupled at a second, opposing end to a funnel at or proximal to a distal end of the catheter tube. In this way, the sleeve may define an internal volume about the catheter tube between the wetting mechanism at or proximal to the tip end of the catheter tube, and a funnel at or proximal to a distal end of the catheter tube.

The catheter may be configured such that fluid within the wetting chamber of the wetting mechanism is able to flow into and along the sleeve to wet the catheter tube, in use. For example, in some embodiments the housing of the wetting mechanism comprises an aperture or opening therein allowing fluid within the wetting chamber to flow into the sleeve. The wetting mechanism may be configured such that the aperture or opening in the housing may be blocked with the stopper in the first position and unblocked with the stopper in the second position. Advantageously, "unlocking" the catheter tube may additionally release the wetting fluid into the sleeve to wet the outer surface of the tube.

The catheter may comprise a urinary catheter. The catheter may comprise a female urinary catheter, but is preferably a male urinary catheter. The catheter may comprise a single-use catheter. The catheter may comprise an intermittent urinary catheter.

The catheter tube may have a length of up to (and possibly upwards) of 35 cm. The catheter tube may be up to or at least 20 cm, up to or at least 25 cm, up to or at least 30 cm, up to or at least 35 cm, or up to or at least 40 cm, in length, for example. In embodiments, the catheter tube may be more than 40 cm in length. In preferred embodiments, the catheter tube is between 25-35 cm, in length. Male catheters typically have a catheter tube of such lengths and would be less suited to mechanisms which wet the catheter tube from the distal end (as opposed to the tip end as in the present invention), as the fluid may not adequately cover the entire length of the tube. This potentially results in the tip end being wetted last (or not at all if there is insufficient fluid), which is undesirable since the tip end will be introduced into the urethra first and is hence most likely to cause injury if inadequately wetted before use. Accordingly, the invention is particularly suited to male catheters.

The catheter tube may comprise, may be integrated with, or may be coated with a hydrophilic component. The hydrophilic component may be configured to provide a low friction surface (e.g. outer surface) of the catheter tube upon application of the wetting fluid. The hydrophilic component may comprise a hydrophilic polymer, for example.

According to an aspect of the invention there is provided a sealed packaged catheter according to the preceding aspect of the invention, wherein the wetting mechanism is operably coupled at or proximal to the tip end of the catheter tube within the sealed package.

According to an aspect of the invention there is provided a method for wetting a tube of a catheter using the wetting mechanism of any aspect described herein, the method comprising: moving the stopper from a first position to a second position; and subsequently introducing the tip end of the catheter tube into the wetting chamber and moving it therethrough, thereby wetting the at least a portion of an outer surface of the catheter tube.

Moving the stopper from the first position to the second position may cause, or allow for, release of a wetting fluid from a holding chamber of the housing to the wetting chamber. Additionally or alternatively, moving the stopper from the first position to the second position may cause, or allow for, release of a wetting fluid from the wetting chamber into a sleeve of the catheter provided about the catheter tube.

In some embodiments the stopper comprises a plug and method may comprise at least partly withdrawing the plug from the wetting mechanism. The method may comprise at least partly withdrawing the plug from the wetting chamber to cause release of the fluid from a holding chamber into the wetting chamber. The method may comprise fully withdrawing the plug from the wetting mechanism.

DETAILED DESCRIPTION OF THE INVENTION

In order that the invention may be more clearly understood one or more embodiments thereof will now be described, by way of example only, with reference to the accompanying drawings, of which.

In general, the present invention relates to a catheter 10, 310, and specifically to a wetting mechanism 20, 120, 220, 320 configured for use to wet a tube 12, 312 of the catheter 10, 310, in use.

The Figures illustrate a series of embodiments of the invention. Where equivalent components are present between embodiments, like reference numerals have been used.

Figure 1:
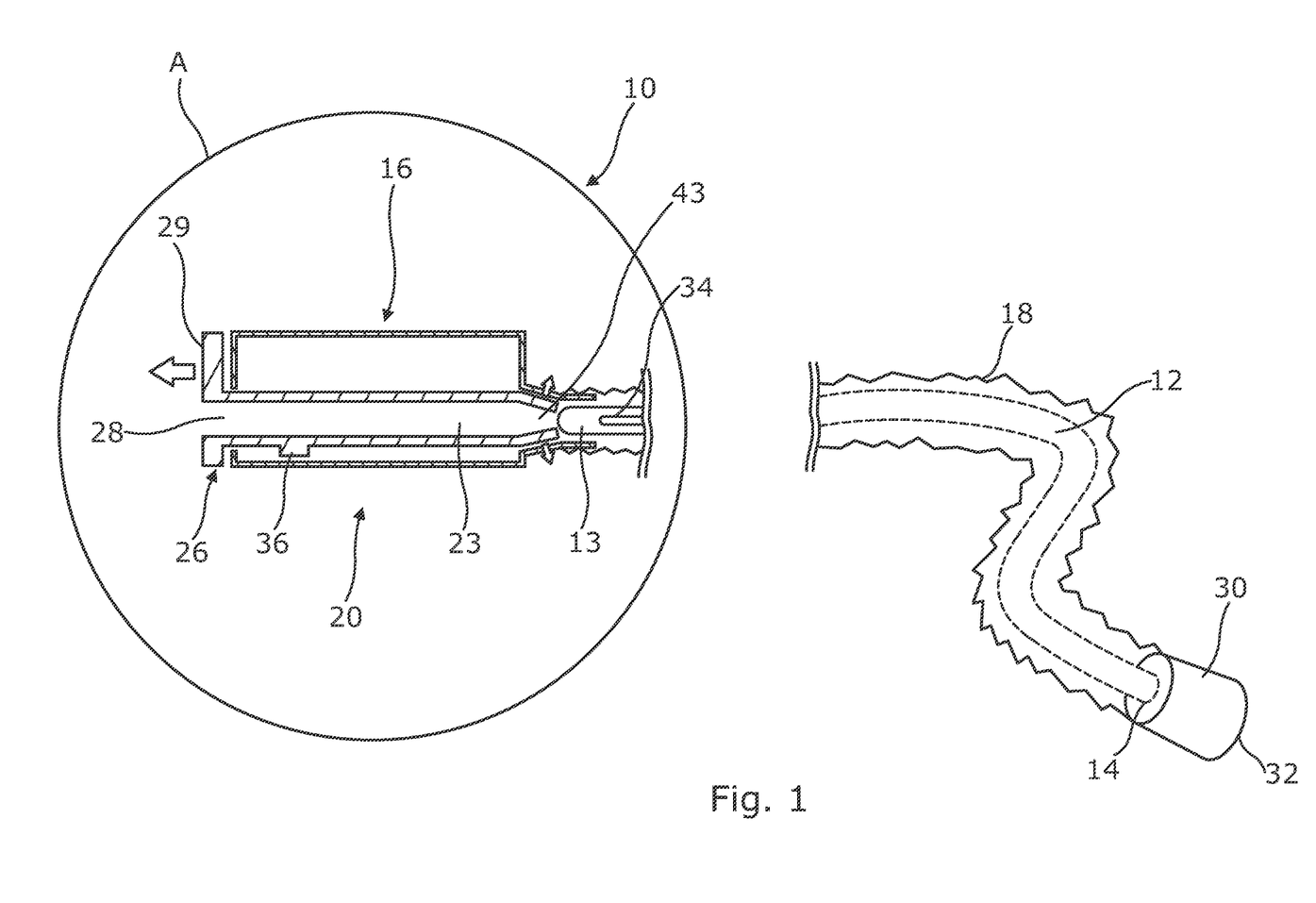
FIG. 1 is a schematic overview of a first embodiment of the invention.
Figure 2A:
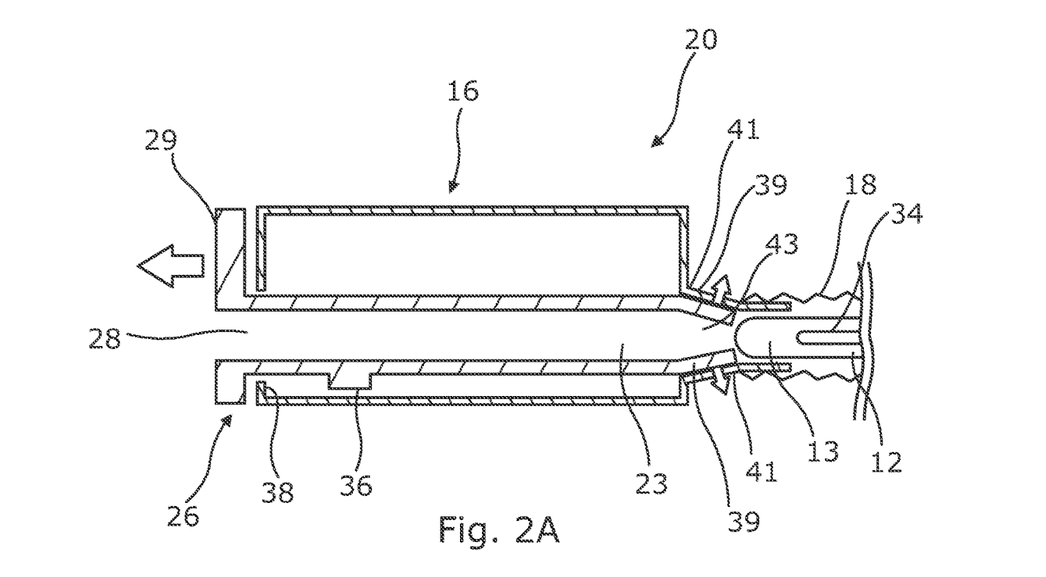
FIGS. 2A and 2B are side cross-sectional schematic views of section A in FIG. 1, illustrating the operational use thereof.
Figure 2B:
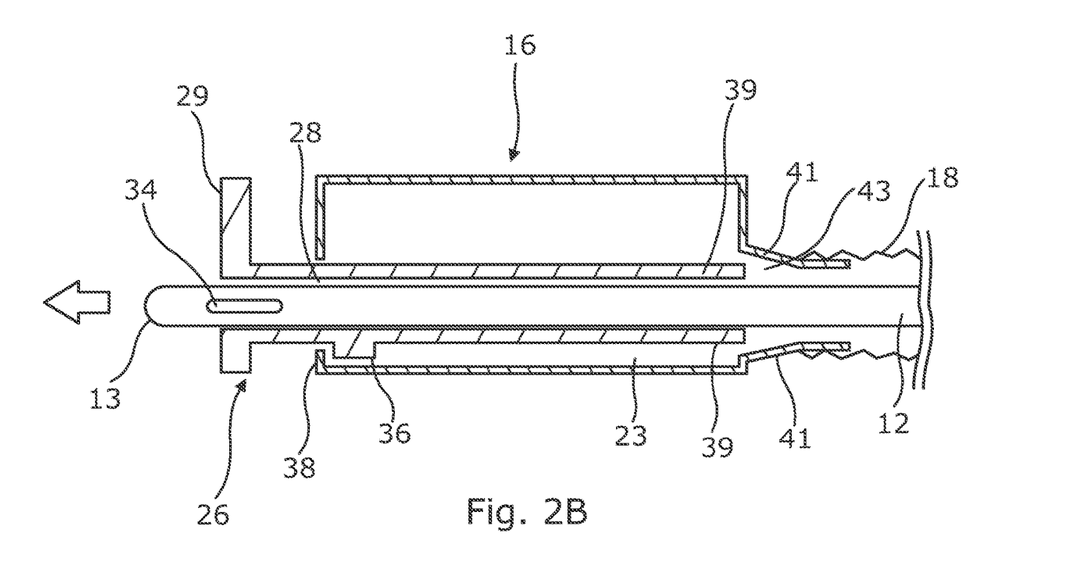

FIGS. 1-2B illustrate a first embodiment of a wetting mechanism 20 for use in wetting a tube 12 of a catheter 10.

The catheter 10 includes the catheter tube 12, with the wetting mechanism 20 provided at a tip end 13 (proximal end) of the catheter tube 12 and a funnel 30 at a distal end 14 of the catheter tube 12. A sleeve 18 is provided between the wetting mechanism 20 and the funnel 30, enclosing the catheter tube 12 therebetween. Here, the sleeve 18 is formed of a flexible film material and is coupled at a first end to a housing 16 of the wetting mechanism 20 and at a second end to the funnel 30. In this way, the sleeve 18 defines an internal volume about the catheter tube 12 into which fluid may be introduced to wet the outer surface of the catheter tube 12.

As mentioned above, the catheter tube 12 has a tip end 13 and a distal end 14. The tip end 13 includes a tip for insertion of the catheter tube 12 into a canal, vessel, passageway, body cavity, etc. for removal of fluid therefrom. Here, the catheter 10 comprises a male urinary catheter 10 with the tip configured for insertion into a male patient's bladder. The tip end 13 of the catheter tube includes an aperture 34 therein for allowing for fluid to enter the interior of the catheter tube 12. The distal end 14 of the catheter tube 12 is provided within the funnel 30. Specifically, the distal end 14 of the catheter tube 12 is located within the funnel 30 and opens into the funnel 30, which defines a fluid outlet 32 which serves as an outlet for discharging fluid from within the catheter tube 12. The catheter tube 12 itself comprises a hydrophilic coating which acts to provide a low friction outer surface of the catheter tube 12 upon application of a wetting fluid.

The wetting mechanism 20 includes a tubular housing 16 positioned (at least initially) at a tip end 13 of the catheter tube 12. The housing 16 includes a wetting chamber 23 which contains a volume of fluid (not shown) therein for wetting the catheter tube 12. The wetting chamber has an inlet 43 at a first end and an outlet 28 at a second end, defining an inlet and an outlet for the catheter tube 12. In use, and as is described herein, the fluid is brought into contact with the catheter tube 12 upon movement of the catheter tube 12 through the wetting chamber 23, and optionally through fluid flowing into the sleeve 18 about the catheter tube 12.

The wetting mechanism 20 comprises a stopper in the form of a plug 26. As is described herein, the plug 26 is configured to control (i.e. prevent or allow) movement of the catheter tube 12 through the wetting chamber 23. In the illustrated embodiment, the plug 26 is substantially cylindrical, and defines an outlet 28 of the housing 16 through which, in use, the catheter tube 12 can be moved, although other profiles are equally applicable. As shown in FIGS. 1 and 2A, the plug 26 is initially located within the wetting chamber 23 with a portion of the plug 26 received within the inlet 43 of the wetting chamber 23. Specifically, flexible end portions, here cantilevered end portions 39 are provided in contact with surfaces 41 on the housing 16 at the inlet 43. The surfaces 41 are sloped so as to urge the cantilevered portions 39 inwards towards one another to partially block the inlet 43. This is herein referred to as a first position or first configuration of the plug 26, corresponding to a position wherein the catheter tube 12 is prevented from being introduced into the wetting chamber 23 through the inlet 43. A lip 29 is provided at the opposite end of the plug 26 which defines an interaction point for the user, specifically for the user to grip the lip 29 to provide leverage for moving the plug 26.

FIGS. 2A-2B illustrate the operational use of the wetting mechanism 20. As set out above, initially the wetting mechanism 20 is provided in the first configuration with the plug 26 in a first position blocking the inlet 43 of the wetting chamber 23 (FIG. 2A). In order to activate the wetting mechanism 20, the plug 26 is partially displaced from (i.e. pulled out from) the wetting chamber 23 to a second position (FIG. 2B). In doing so, the plug 26 is moved to a position where the inlet 43 is no longer blocked, specifically by withdrawing the cantilevered end portions 39 from the inlet 43. The flexible and resilient nature of the end portions 39 is such that the end portions are biased to the configuration shown in FIG. 2B in which they are open wider and wherein the inlet 43 is unblocked, and the catheter tube 12 is able to be moved through a channel defined through the plug 26.

A notch 36 is provided on an outer circumferential surface of the plug 26 to define the extent to which the plug 26 can be removed from the wetting chamber 23. Specifically, the notch 36 provides a point of contact between the plug 26 and a circumferentially inwardly extending flange 38 at the end of the housing 16.

Subsequently, the catheter tube 12 may be moved through the wetting chamber 23, bringing the catheter tube 12 into contact with the wetting fluid and hence wetting an outer surface of the catheter tube 12. Once the tip end 13 of the catheter tube 12 is moved beyond the lip 29 in the plug 26, and out through an outlet 28 of the housing 16, the tip end 13 then becomes exposed for insertion by the user. The housing 16 then acts as a gripping element for the user to direct the catheter tube 12, in use, as the user may then use the housing 16 to easily direct the exposed tip end 13 of the catheter tube 12 without contacting the tube 12 directly.

Withdrawal of the plug 26 from the wetting chamber 23 to the second position (FIG. 2B)—i.e. withdrawing the cantilevered end portions 39 from the inlet 43 may allow for fluid contained within the wetting chamber 23 to flow through the inlet 43 and into the sleeve 18.

Figure 3A:
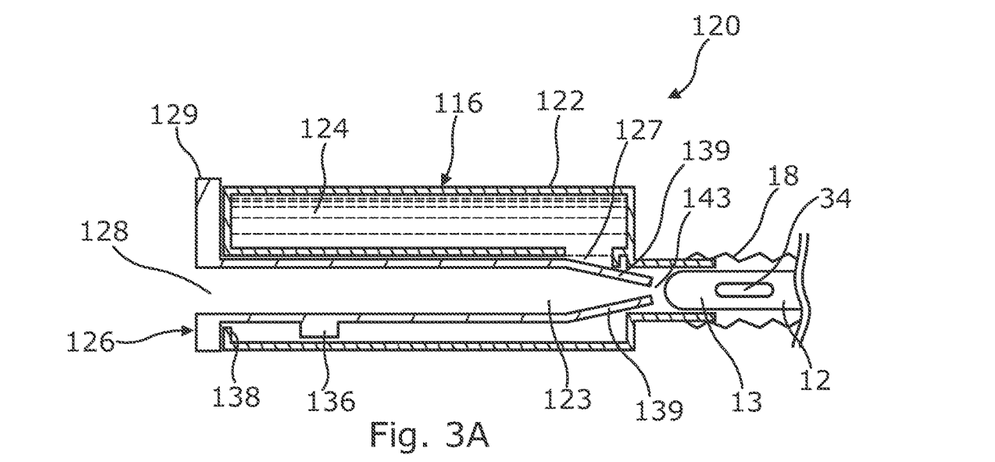
FIGS. 3A-3C are a series of cross-sectional schematic views illustrating the operational use of a second embodiment.
Figure 3B:
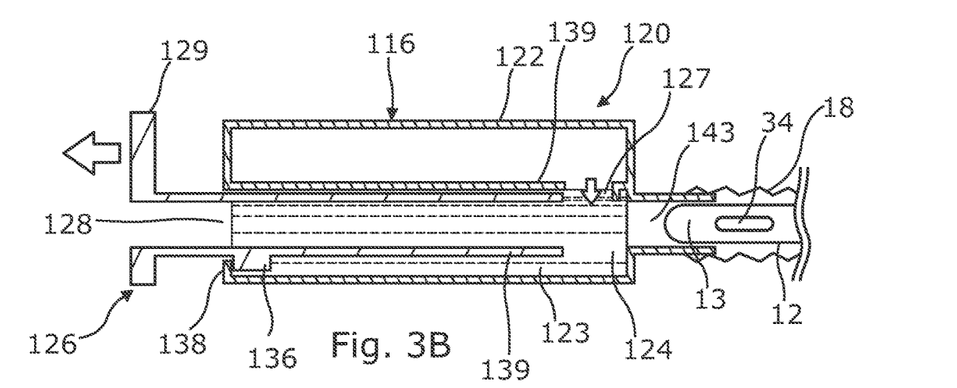
Figure 3C:
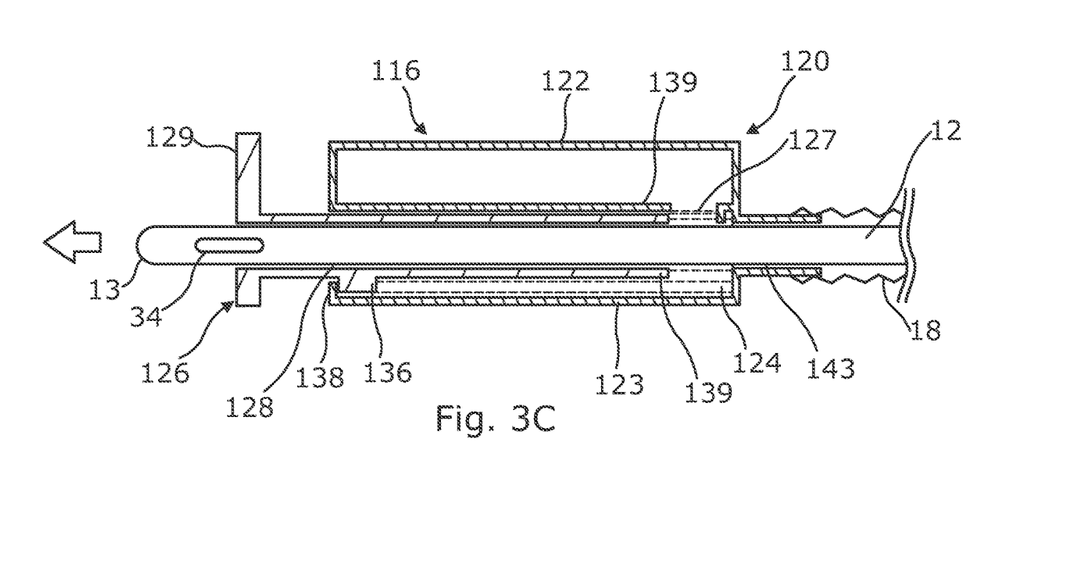

A variant of wetting mechanism 20 is shown in FIGS. 3A-3C. Specifically, these figures show a wetting mechanism 120 configured in substantially the same way as wetting mechanism 20 shown in the preceding Figures. Wetting mechanism 120 differs in that it comprises a housing 116 which, in addition to a wetting chamber 123, includes a holding chamber 122. The holding chamber 122 and wetting chamber 123 are fluidly connected to one another by an opening 127 in the housing.

As shown, the holding chamber 122 contains a volume of fluid 124 therein for wetting the catheter tube 12 and, in use, the fluid 124 may be released from said holding chamber 122 into the wetting chamber 123 upon movement of a plug 126. By releasing the fluid 124 into the wetting chamber 123, and subsequently moving the catheter tube 12 through the wetting chamber 123, an outer surface of the catheter tube 12 may be wetted using the fluid 124.

Wetting mechanism 120 may function in essentially the same way as wetting mechanism 20, with a plug 126 provided which is movable between two positions to prevent or allow movement of the catheter tube 12 through the wetting chamber 123 in dependence on the position of the plug 126. However, here movement of the plug 126 to the second position additionally controls release of the wetting fluid 124 from the holding chamber 122. Specifically, movement of the plug 126 to the second position unblocks opening 127 allowing the fluid 124 contained within the holding chamber 124 to be released into the wetting chamber 123. Advantageously, having the fluid 124 stored in a separate holding chamber 122 until (or as close as possible to) the point of use of the catheter 10 reduces the contact time of most components of the catheter 10 with the fluid 124, which may be advantageous in terms of shelf-life of the catheter 10.

Figure 4A:
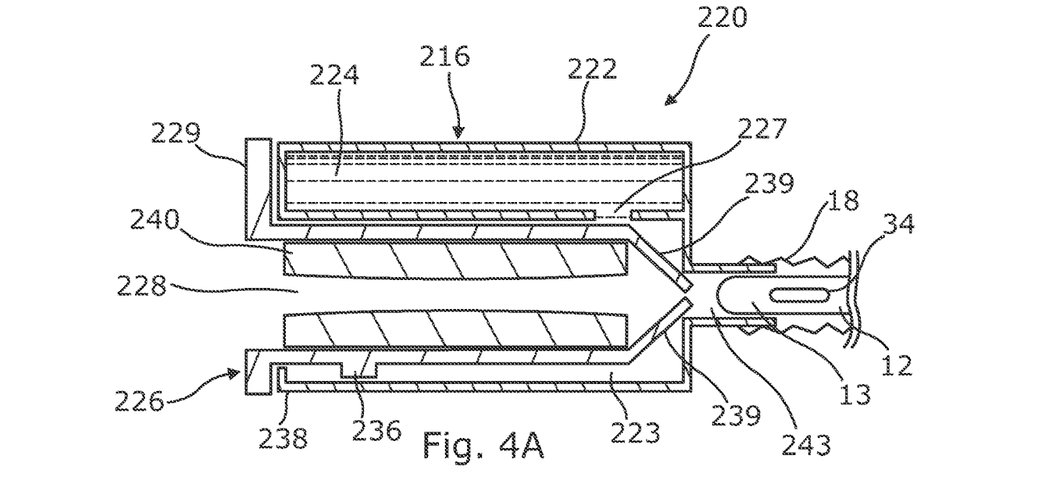
FIGS. 4A-4C are a series of further cross-sectional schematic views illustrating the operational use of a third embodiment.
Figure 4B:
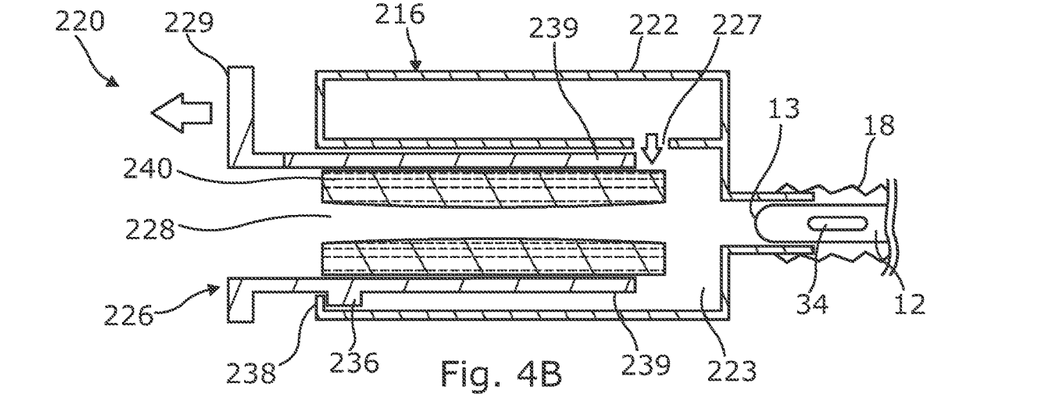
Figure 4C:
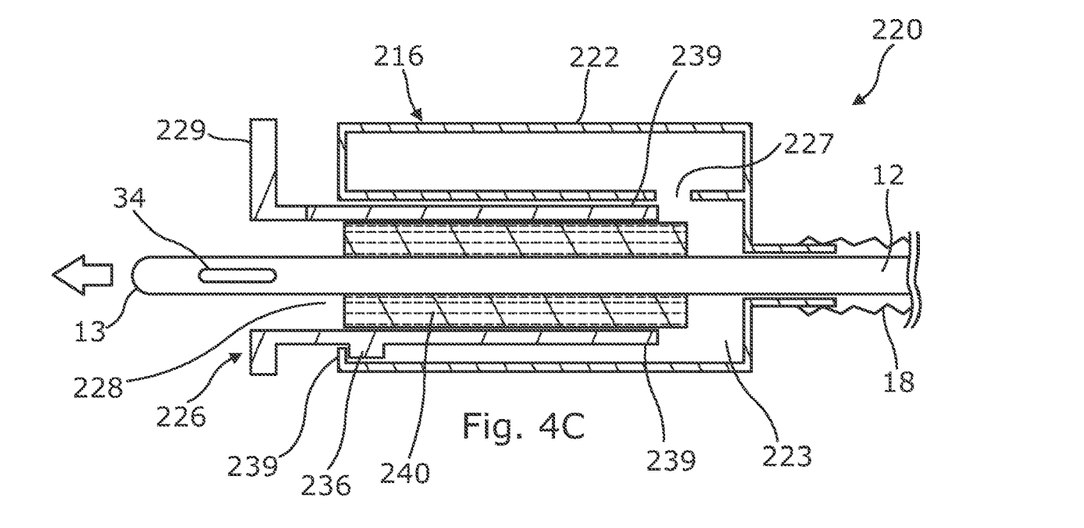

A variant of wetting mechanism 120 is shown in FIGS. 4A-4C. Specifically, these figures show a wetting mechanism 220 configured in substantially the same way as wetting mechanism 120 shown in FIGS. 3A-3C. Wetting mechanism 220 differs in that it additionally includes a wetting applicator in the form of a foam conduit 240 positioned within the wetting chamber 223. As is discussed in detail herein, the foam conduit 240 is configured to hold fluid released into the wetting chamber 240 from the holding chamber 222 and is configured to control application of the fluid to the catheter tube 12, in use, as the catheter tube 12 is moved through the wetting chamber 223.

Wetting mechanism 220 functions in essentially the same way as wetting mechanism 20, with a plug 226 provided which is movable between two positions to control both the movement of the catheter tube 12 through the wetting chamber 223, and the release of the wetting fluid 224 from the holding chamber 222 into the wetting chamber 223. Here, upon movement of the plug 226 to the second position, thereby unlocking the opening 227, the fluid 224 contained within the holding chamber 222 is released onto the foam conduit 240. The foam conduit 240 stores the fluid 224 released onto it for subsequent application to the catheter tube 12. Specifically, the foam conduit 240 defines a channel within the wetting chamber 223 through which the catheter tube 12 is able to move through and be brought into contact with the foam conduit 240. The foam conduit 240 is configured such that fluid held therein is released upon movement of the catheter tube 12 through the defined channel by virtue of the catheter tube 12 coming into contact with the foam conduit 240 and applying a pressure thereto. A wetting applicator of this type may advantageously ensure that the wetting fluid 224 is applied evenly across the outer surface of the catheter tube 12.

Figure 5:
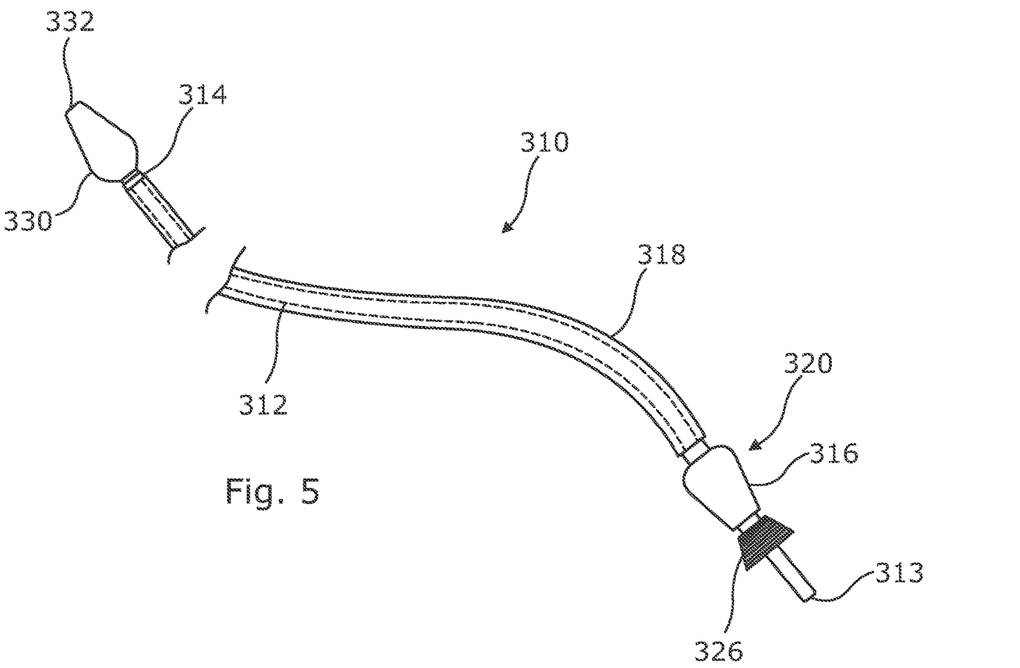
FIG. 5 is a perspective view of a fourth embodiment of the invention.
Figure 6A:
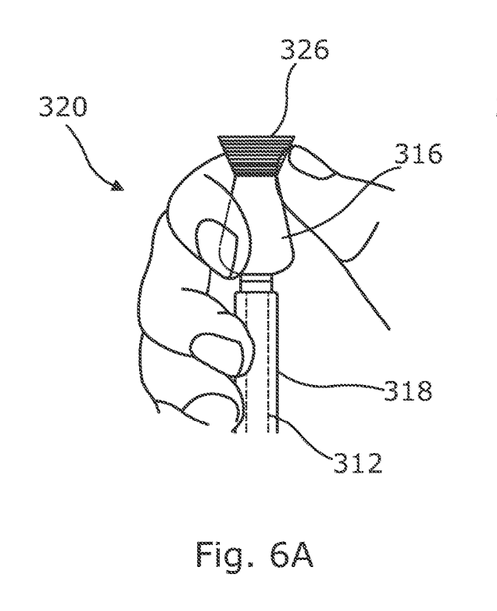
FIGS. 6A-6B are a pair of side views illustrating the operational use of the embodiment shown in FIG. 5.
Figure 6B:
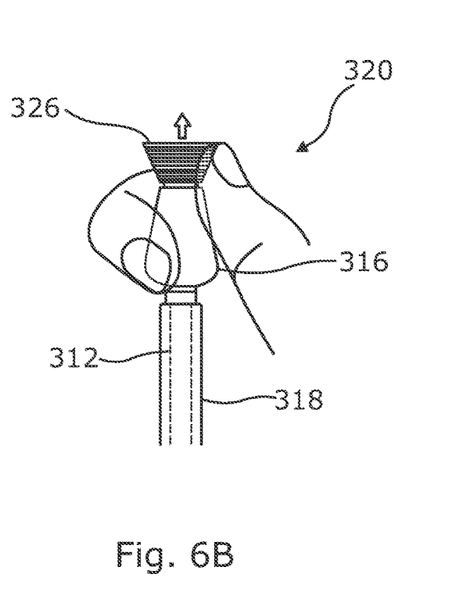

FIGS. 5-6B illustrate further embodiments of a catheter 310 and wetting mechanism 320 operable to wet a tube 312 of the catheter 310, in use.

As with catheter 10, the catheter 310 includes the catheter tube 312, with the wetting mechanism 320 provided at a tip end 313 of the catheter tube 312 and a funnel 330 at a distal end 314 of the catheter tube 312. A sleeve 318 is provided between the wetting mechanism 320 and the funnel 330, enclosing the catheter tube 12 therebetween.

The tip end 313 of the catheter 310 includes a tip for insertion of the catheter tube 312 into a canal, vessel, passageway, body cavity, etc. for removal of fluid therefrom. Here, the catheter 310 comprises a male urinary catheter 310 with the tip configured for insertion into a male patient's bladder. The distal end 314 of the catheter tube 312 is provided within the funnel 330. Specifically, the distal end 314 of the catheter tube 312 is located within the funnel 330 and opens into the funnel 330 which defines a fluid outlet 332 which serves as an outlet for discharging fluid from within the catheter tube 312. The funnel 330 is shaped to aid the user's control over the direction of discharge of the fluid from the catheter tube 312. The catheter tube 312 itself comprises a hydrophilic coating which acts to provide a low friction outer surface of the catheter tube 312 upon application of a wetting fluid.

The wetting mechanism 320 is similar in configuration to wetting mechanisms 120, 220 described herein, and may be of the nature of, with the same features as, any of the embodiments of the preceding Figures. It includes a housing 316 positioned (at least initially) at the tip end 313 of the catheter tube 312. The housing 316 includes a holding chamber (not shown) which contains a volume of fluid therein for wetting the catheter tube 312. In use, and as is described herein, the fluid may be released from said holding chamber into a wetting chamber (not shown) of the housing 316 under the operation of a plug 326. Additionally, the plug 326 is operable to control the ability of the catheter tube 312 being moved through the wetting chamber of the housing 316 in the same way as plugs 26, 126 and 226 of the preceding Figures. As with the other embodiments described herein, by unblocking the catheter tube 312, releasing the fluid into the wetting chamber, and subsequently moving the catheter tube 312 through the wetting chamber, an outer surface of the catheter tube 312 may be wetted using the fluid.

The plug 326 is moveable from the position shown in FIG. 6A (a first position) to the position shown in FIG. 6B (a second position). Movement from the first position to the second position both unblocks an inlet (not shown) of the housing 316 allowing the catheter tube 312 to be introduced and moved through the housing 316, and also causes release of the wetting fluid from the holding chamber into the wetting chamber.

In this embodiment, the plug 326 comprises a conical cross section, with a ridged exterior surface defining an interaction surface for the user. The housing 316 is also substantially conical in profile, and is positioned in such a way to define an hourglass-shaped configuration of the housing 316 and plug 326. This arrangement is particularly beneficial as it may allow for operation of the plug 326 using only one hand, as shown in FIGS. 10A and 10B. Specifically, and as shown in these Figures, the user may grip the housing 316 and plug 326 between their thumb and forefinger, before using their thumb to push or "pop" the plug 326 upwards (in the orientation shown in the Figures). Moreover, the conical plug 326 has a cup like end, which eases location of the housing 316 over the tip of the penis to aid insertion of the catheter tube 312 into the urethra, in use.

In a variant, the stopper (e.g. the plug 26, 126, 326) may alternatively be rotatable between first and second positions/configurations. For example, rotation of the plug 26, 126, 326 (rather than linear movement) may unblock the inlet 43, 143, 243 of the wetting chamber 23, 123, 223, and optionally may align an opening in the stopper unblock an opening 127, 227 or valve in the housing 116, 316 allowing for the release of the wetting fluid into the wetting chamber.

In a variant, the wetting mechanism (e.g. mechanism 20) may be configured to retain the plug 26 in the first and/or second position. For example, the wetting mechanism 20 may be configured to retain the plug 26 in the first position, preventing introduction of the catheter tube 12, and optionally preventing release of the fluid from the holding chamber 22, unless positively acted on by a user. This may be provided, for example, in the form of an abutment between a frangible portion on the plug 26 and/or on the housing 16 configured to break upon application of a force by the user. In this way, the plug 26 may "snap" or "click" in overcoming said abutment to provide tactile and/or audible feedback for the user. The wetting mechanism 20 may be configured such that, in the second position at least a portion of the plug 26 is provided in an abutting relationship with a further component of the wetting mechanism (e.g. the housing 16)

preventing further movement of the plug 26 and thereby preventing the plug 26 being returned to the first position.

In a variant, the housing (e.g. housing 16) may include a valve arrangement or the like preventing the wetting fluid from being released from the housing. For example, the housing can include a valve arrangement at the inlet 43 and/or at the outlet 28. The valve arrangement may be configured to allow the catheter tube 12, 312 to be moved therethrough.

In a variant, the wetting applicator can comprise a sponge or wicking material, operable to absorb the wetting fluid, in use, or may comprise a baffle arrangement.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The one or more embodiments are described above by way of example only. Many variations are possible without departing from the scope of protection afforded by the appended claims.

The invention claimed is:

1. A wetting mechanism for wetting a tube of a male urinary catheter, the wetting mechanism comprising:
   a housing forming a gripping element for the catheter, the housing being configured to be positioned initially at or proximal to the tip end of the catheter tube;
   wherein the housing comprises a wetting chamber into which at least a portion of the catheter tube is able to be introduced and be moved therethrough to wet the catheter tube in use; and
   wherein the wetting mechanism comprises a stopper moveable between a first position in which the stopper prevents the tip end of the catheter tube being moved through the wetting chamber and a second position in which stopper does not prevent the tip end of the catheter tube being moved through the wetting chamber.

2. A wetting mechanism as claimed in claim 1, wherein the tip end of the catheter tube is, at least initially, disposed outside the wetting chamber.

3. A wetting mechanism as claimed in claim 1, wherein the stopper is linearly moveable between first and second positions.

4. A wetting mechanism as claimed in claim 1, wherein the stopper comprises a plug configured to be at least partly withdrawn from the wetting mechanism in moving from the first position to the second position.

5. A wetting mechanism as claimed in claim 1, wherein the wetting chamber comprises an inlet through which the catheter tube is able to be introduced into the wetting chamber, and wherein the stopper at least partially blocks the inlet in the first position.

6. A wetting mechanism as claimed in claim 5, configured such that movement of the stopper from the first position to the second position unblocks the inlet, thereby allowing for the catheter tube to be introduced into the wetting chamber.

7. A wetting mechanism as claimed in claim 5, wherein at least a portion of the stopper is received within the inlet of the wetting chamber with the stopper in the first position.

8. A wetting mechanism as claimed in claim 7, wherein an end of the stopper is received with the inlet of the wetting chamber with the stopper in the first position.

9. A wetting mechanism as claimed in claim 8, wherein the end of the stopper comprises a flexible and/or compressible material configured to be compressed within the inlet of the wetting chamber.

10. A wetting mechanism as claimed in claim 8, wherein the end of the stopper comprises one or more cantilevered portions operable to bend or flex when at least partially received within the inlet of the wetting chamber.

11. A wetting mechanism as claimed in claim 10, wherein the end of the stopper comprises a plurality of cantilevered portions, the plurality of cantilevered portions being configured to bend or flex in a direction substantially towards one another when at least partially received within the inlet of the wetting chamber.

12. A wetting mechanism as claimed in claim 8, wherein, in use, movement of the stopper from the first position to the second position withdraws the end of the stopper from the inlet of the wetting chamber.

13. A wetting mechanism as claimed in claim 12, wherein withdrawal of the stopper releases any external force provided on the end of the stopper, thereby allowing the compressed, bent or flexed portion of the stopper to move to a position where it does not prevent the tip end of the catheter tube from being introduced into the wetting chamber.

14. A wetting mechanism as claimed in claim 1, wherein the stopper is tubular defining a channel therethrough, and wherein the catheter tube may be moved through said channel, in use.

15. A wetting mechanism as claimed in claim 1, wherein the wetting chamber comprises a volume of fluid contained therein.

16. A wetting mechanism as claimed in claim 1, wherein the housing comprises a holding chamber containing a volume of fluid therein.

17. A wetting mechanism as claimed in claim 16, wherein the stopper forms a fluid release control component for the wetting mechanism configured to control release of fluid contained within the holding chamber to the wetting chamber.

18. A wetting mechanism as claimed in claim 17, wherein the stopper is configured such that, in the first position, the stopper prevents release of fluid from the holding chamber, and in the second position, the stopper allows release of fluid from the holding chamber into the wetting chamber.

19. A wetting mechanism of claim 1, configured to retain the stopper in the first and/or second position.

20. A wetting mechanism of claim 1, comprising a wetting applicator positioned within the wetting chamber, the wetting applicator being configured to hold wetting fluid and to control application of the fluid to the catheter tube, in use, as the catheter tube is moved through the wetting chamber.

21. An apparatus comprising the wetting mechanism of claim 1, further comprising a male urinary catheter, wherein the wetting mechanism is operably coupled at or proximal to the tip end of the catheter tube for wetting the catheter tube, in use.

22. The apparatus of claim 21, comprising a sealed package, wherein the wetting mechanism is operably coupled at or proximal to the tip end of the catheter tube within the sealed package.

23. A wetting mechanism for wetting a tube of a male urinary catheter, the wetting mechanism comprising:

a housing forming a gripping element for the catheter, the housing being configured to be positioned initially at or proximal to a tip end of the catheter tube, wherein the housing comprises a wetting chamber into which at least a portion of the catheter tube is able to be introduced and be moved through the wetting chamber to wet the catheter tube; and a stopper moveable between a first position in which the stopper prevents the tip end of the catheter tube being moved through the wetting chamber, and a second position in which the stopper does not prevent the tip end of the catheter tube being moved through the wetting chamber;

wherein an end of the stopper comprises a plurality of cantilevered portions, the plurality of cantilevered portions being configured to flex toward one another when at least partially received within an inlet of the wetting chamber.

24. The wetting mechanism of claim 23, wherein movement of the stopper from the first position to the second position withdraws the plurality of cantilevered portions from the inlet of the wetting chamber.

25. A wetting mechanism for wetting a tube of a male urinary catheter, the wetting mechanism comprising:

a housing forming a gripping element for the catheter, the housing being configured to be positioned initially at or proximal to a tip end of the catheter tube, wherein the housing comprises a wetting chamber into which at least a portion of the catheter tube is able to pass through for wetting of the catheter tube; and a tubular stopper moveable between a first position in which the tubular stopper prevents the tip end of the catheter tube being moved through the wetting chamber and a second position in which the tubular stopper does not prevent the tip end of the catheter tube being moved through the wetting chamber, the tubular stopper comprising a channel extending therethrough.

26. The wetting mechanism of claim 25, wherein the catheter tube is operable to move through the channel when the tubular stopper is in the second position.

27. The wetting mechanism of claim 25, wherein an end of the tubular stopper is operable to be compressed within the inlet of the wetting chamber when the tubular stopper is in the first position.

* * * * *